United States Patent
Khalifa et al.

(10) Patent No.: US 10,039,749 B1
(45) Date of Patent: Aug. 7, 2018

(54) SUBSTITUTED PYRAZOLE DERIVATIVES (71) Applicant: KING SAUD UNIVERSITY, Riyadh (SA)

(72) Inventors: Nagy Mahmoud Hassan Khalifa, Riyadh (SA); Mohamed A. Al-Omar, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/871,943

(22) Filed: Jan. 15, 2018

(51) Int. Cl.
*A61K 31/4155* (2006.01)
*A61P 35/00* (2006.01)
*C07D 403/06* (2006.01)

(52) U.S. Cl.
CPC .......... *A61K 31/4155* (2013.01); *A61P 35/00* (2018.01); *C07D 403/06* (2013.01)

(58) Field of Classification Search
None
See application file for complete search history.

(56) References Cited

U.S. PATENT DOCUMENTS

| | | | |
|---|---|---|---|
| 4,325,962 | A | 4/1982 | Rainer |
| 8,357,673 | B2 | 1/2013 | Cankar et al. |
| 8,455,694 | B2 | 5/2013 | Zhang et al. |
| 9,340,505 | B2 | 5/2016 | Goguen et al. |
| 9,522,914 | B2 | 12/2016 | Yoshinaga et al. |
| 2012/0302581 | A1 | 11/2012 | Ratner et al. |

OTHER PUBLICATIONS

CAPLUS printout of Hozien et al., A convenient one-pot synthesis of pyrazolo[3,4-d]pyrimidines and s-triazolo[3,4-b][1,3,5] thiadiazines. Zeitschrift fuer Naturforschung, B: Chemical Science, 1997, 52, 1401-1412.*
Alam R., Wahi D., Singh R., Sinha D., Tandon V., Grover A., Rahisuddin., "Design, synthesis, cytotoxicity, HuTopoIIα inhibitory activity and molecular docking studies of pyrazole derivatives as potential anticancer agents". Bioorganic Chemistry 2016, 69: 77-90. Doi: 10.1016/j.bioorg.2016.10.001.
Fu-Qiang W., Hui Y., Bin H., Yong-Kang J., Shi-Yao M., Chao Z., Hong-Min L., Feng-Wu L., "A novel domino approach for synthesis of indolyl tetrahydropyrano [4,3-c]pyrazole derivatives as anticancer agents". Tetrahedron 2016, 72: 5769-5775.
Peng-Cheng L., Huan-Qiu L., Juan S., Yang Z., Hai-Liang Z., "Synthesis and biological evaluation of pyrazole derivatives containing thiourea skeleton as anticancer agents". Bioorganic & Medicinal Chemistry 2010, 18: 4606-4614.
Mohamed A.A., Rania B.B., Hany A.O., "Design, synthesis and biological evaluation of some novel benzothiazole/benzoxazole and/or benzimidazole derivatives incorporating a pyrazole scaffold as antiproliferative agents". Bioorganic Chemistry 2017, 74: 82-90.
Shi JB., Tang WJ., Qi XB., Li R., Liu XH., "Novel pyrazole-5-carboxamide and pyrazole-pyrimidine derivatives: synthesis and anticancer activity". European Journal of Medicinal Chemistry 2015, 90: 889-896.
Wang M., Xu S., Lei H., Wang C., Xiao Z., Jia S., Zhi J., Zheng P., Zhu W., "Design, synthesis and antitumor activity of Novel Sorafenib derivatives bearing pyrazole scaffold". Bioorganic & Medicinal Chemistry 2017, 25: 5754-5763.
Eurtivong C., Reynisdóttir I., Kuczma S., Furkert DP., Brimble MA., Reynisson J., "Identification of anticancer agents based on the thieno[2,3-b]pyridine and 1H-pyrazole molecular scaffolds". Bioorganic & Medicinal Chemistry 2016, 24: 3521-3526.
Hafez HN., El-Gazzar AR., Al-Hussain SA., "Novel pyrazole derivatives with oxa/thiadiazolyl, pyrazolyl moieties and pyrazolo[4,3-d]-pyrimidine derivatives as potential antimicrobial and anticancer agents". Bioorganic & Medicinal Chemistry Letters 2016, 26: 2428-2433.
Li X., Lu X., Xing M., Yang XH., Zhao TT., Gong HB., Zhu HL., "Synthesis, biological evaluation, and molecular docking studies of N,1,3-triphenyl-1H-pyrazole-4-carboxamide derivatives as anticancer agents". Bioorganic & Medicinal Chemistry Letters 2012, 22: 3589-3593.
Dawood KM., Eldebss TM., El-Zahabi HS., Yousef MH., Metz P., "Synthesis of some new pyrazole-based 1,3-thiazoles and 1,3,4-thiadiazoles as anticancer agents". European Journal of Medicinal Chemistry 2013, 70: 740-749.
Kumar H., Saini D., Jain S., Jain N., "Pyrazole scaffold: a remarkable tool in the development of anticancer agents". European Journal of Medicinal Chemistry 2013, 70: 248-258.
Ramirez-Prada J., Robledo SM., Velez ID., Crespo MDP., Quiroga J., Abonia R., Montoya A., Svetaz L., Zacchino S., Insuasty B., "Synthesis of novel quinoline-based 4,5-dihydro-1 H-pyrazoles as potential anticancer, antifungal, antibacterial and antiprotozoal agents". European Journal of Medicinal Chemistry 2017, 131: 237-254.
Salama SK., Mohamed MF., Darweesh AF., Elwahy AH., Abdelhamid IA., "Molecular docking simulation and anticancer assessment on human breast carcinoma cell line using novel bis(1,4-dihydropyrano[2,3-c]pyrazole-5-carbonitrile) and bis(1,4-dihydropyrazolo [4',3':5,6]pyrano[2,3-b]pyridine-6-carbonitrile) derivatives". Bioorganic Chemistry 2017, 71: 19-29.

(Continued)

Primary Examiner — Po-Chih Chen
(74) Attorney, Agent, or Firm — Richard C. Litman (57) ABSTRACT

A substituted pyrazole derivative includes a compound of the formula:

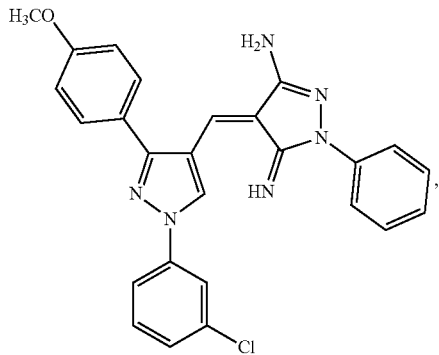

or a pharmaceutically acceptable salt thereof.

12 Claims, 7 Drawing Sheets

(56) References Cited

OTHER PUBLICATIONS

Bandgar BP., Totre JV., Gawande SS., Khobragade CN., Warangkar SC., Kadam PD., "Synthesis of novel 3,5-diaryl pyrazole derivatives using combinatorial chemistry as inhibitors of tyrosinase as well as potent anticancer, anti-inflammatory agents". Bioorganic & Medicinal Chemistry 2010, 18: 6149-6155.

Anis KV., Rajeshkumar NV., Kuttan R., "Inhibition of chemical carcinogenesis by berberine in rats and mice". J Pharm Pharmacol. 2001, 53(5): 763-8.

Conn, HJ., Darrow MA. & Emme VM., (1960) Williams & winlkins Co., Baltimore, 2nd edition, pp. 200.

Cuevas A., Febrero M., Fraiman R., "An anova test for functional data". Comput. Statist. Data Anal. 2004, 47: 111-122.

Swenberg JA., Hoel DG., Magee PN., "Mechanistic and statistical insight into the large carcinogenesis bioassays on N-nitrosodiethylamine and N-nitroso-dimethylamine". Cancer Res. 1991, 51: 6409-6414.

Abdel-Rahman, R.M., et al., "Chemical reactivity of 3-hydrazino-5,6-diphenyl-1,2,4-triazine towards π-acceptors activated carbonitriles". Indian Journal of Chemistry. May 2007. vol. 46B. pp. 838-846

\* cited by examiner

FIG. 1

Crizotinib

FIG. 2A

Ruxolitinib

SUBSTITUTED PYRAZOLE DERIVATIVES

BACKGROUND

1. Field

The disclosure of the present patent application relates to substituted pyrazole derivatives, and particularly to (4Z)-4-((1-(3-chlorophenyl)-3-(4-methoxyphenyl)-1H-pyrazol-4yl) methylene)-4,5-dihydro-5-imino-1-phenyl-1H-pyrazol-3-amine with promising anticancer properties for therapeutic treatment against hepatic cancer (HePG-2) cell line.

2. Description of the Related Art

Cancer is one of the most serious health problems, characterized by loss of control of growth leading to death. Chemotherapy is still one of the primary modalities for the treatment of cancer. However, the use of available chemotherapeutics is often limited mainly due to toxicities and drug resistance. Resistance to anticancer drugs may develop in two forms, intrinsic and acquired forms. Developing resistance to chemotherapy can be due to poor uptake of the drug, increased production of the target protein, mutations that block the drug binding to its target, alternative metabolic paths, or efflux systems that expel drugs from the cell. Thus combination of chemotherapies with different targets antagonizes the resistance, increases efficiency and decreases toxicity as well.

Figure 2A:
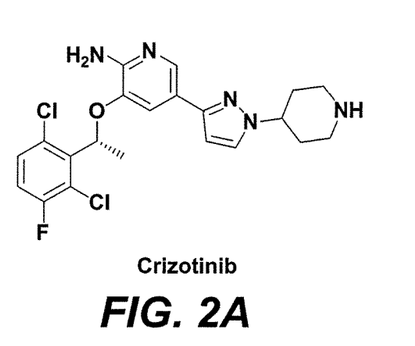
FIG. 2A is the chemical structure for crizotinib.
Figure 2B:
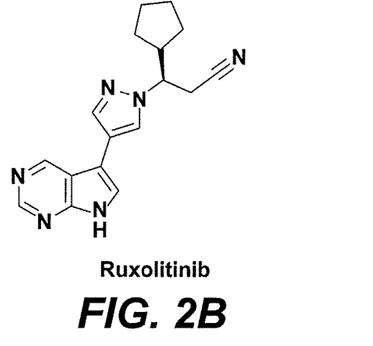
FIG. 2B is the chemical structure for ruxolitinib.

Traditional anticancer drugs work by disrupting the function of DNA. Some of these drugs may act on DNA directly or inhibit the enzymes controlling DNA synthesis. These drugs are mostly non selective and possessing cytotoxicity to both cancer and normal cells. The advances in genetics and molecular biology improve identification of molecular targets that are unique to cancer cells or over expressed on them. The design of agents that will act on these targets promises the development of more selective anticancer agents with less toxic side effects. Among the wide range of compounds tested as potential anticancer agents, pyrazoles were reported to exhibit anticancer activity. Crizotinib and ruxolitinib are important pyrazole based anticancer drugs. FIGS. 2A and 2B show the chemical structures of crizotinib and ruxolitinib, respectively.

Pyrazole derivatives have been shown to exhibit anticancer activity by inhibiting various targets such as topoisomerase II, EGFR, VEGF, HDAC, IGF-1R, Aurora-A kinase, cMet, Tubulin, mTOR, B-raf, ROS 1, CDKs, PI3K, JAK2, and ALK, among others. Thus, incorporation of the pyrazole moiety in drug candidates may provide an important synthetic framework in a drug development process. Moreover, drugs based on heterocyclic compounds containing a 1,2-diaryl substituted pyrazole ring already are known to include bestselling pharmaceutical products. Previously known pyrazole-based drugs include apixaban, celecoxib, fipronil, remogliflozin etabonate, lonazolac, tolpiprazole, deracoxib, and many others. Pyrazole and its synthetic analogs have been shown to exhibit a wide range of beneficial pharmacological effects including, without limitation, anticancer, anti-proliferative, antitumor, antiviral, antimicrobial, antidepressant, anti-inflammatory, anticonvulsant, antihypertensive, tuberculostatic, antileishmanial, antidiabetic, and analgesic effects.

Accordingly, it is desirable to identify and prepare a substituted pyrazole derivative that is non-toxic and effective as an anticancer and anti-tumor agent.

SUMMARY

A substituted pyrazole derivative includes (4Z)-4-((1-(3-chlorophenyl)-3-(4-methoxyphenyl)-1H-pyrazol-4yl)methylene)-4,5-dihydro-5-imino-1-phenyl-1H-pyrazol-3-amine. The substituted pyrazole derivative provides effective anticancer activity, with no marked acute toxicity.

The substituted pyrazole derivative can be prepared by reacting 1-(3-chlorophenyl)-3-(4-methoxyphenyl)-1H-pyrazole-4-carbaldehyde with malononitrile in the presence of a catalyst to provide 2-((1-(3-chlorophenyl)-3-(4-methoxyphenyl)-1H-pyrazol-4-yl)methylene)malononitrile. Subsequent cyclo addition of phenyl hydrazine on the 2-((1-(3-chlorophenyl)-3-(4-methoxyphenyl)-1H-pyrazol-4-yl) methylene) malononitrile completes the synthesis of the substituted pyrazole derivative.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION

Substituted pyrazole derivatives can include (4Z)-4-((1-(3-chlorophenyl)-3-(4-methoxyphenyl)-1H-pyrazol-4yl)

methylene)-4,5-dihydro-5-imino-1-phenyl-1H-pyrazol-3-amine, having the structural formula depicted below:

or a pharmaceutically acceptable salt thereof.

Figure 1:
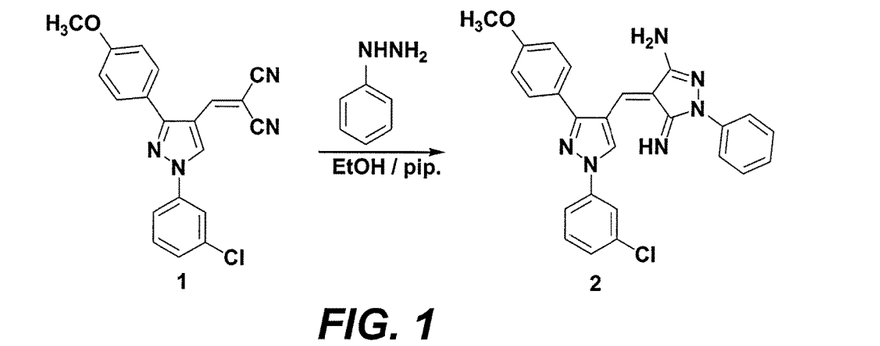
FIG. 1 is a reaction scheme for synthesis of the target compound, (4Z)-4-((1-(3-chlorophenyl)-3-(4-methoxyphenyl)-1H-pyrazol-4-yl)methylene)-4,5-dihydro-5-imino-1-phenyl-1H-pyrazol-3-amine.

As shown in FIG. 1, the substituted pyrazole derivative can be prepared by reacting 1-(3-chlorophenyl)-3-(4-methoxyphenyl)-1H-pyrazole-4-carbaldehyde with malononitrile in the presence of a catalyst to provide 2-((1-(3-chlorophenyl)-3-(4-methoxyphenyl)-1H-pyrazol-4-yl)methylene)malononitrile (1). For example, 1-(3-chlorophenyl)-3-(4-methoxyphenyl)-1H-pyrazole-4-carbaldehyde can be reacted with a reaction mixture including malononitrile, an alcohol, e.g., absolute ethanol, and piperidine as a catalyst to provide 2-((1-(3-chlorophenyl)-3-(4-methoxyphenyl)-1H-pyrazol-4-yl)methylene)malononitrile (1). Subsequent cyclo addition of phenyl hydrazine on 2-((1-(3-chlorophenyl)-3-(4-methoxyphenyl)-1H-pyrazol-4-yl)methylene) malononitrile (1) in the presence of a second reaction mixture including piperidine completes the synthesis of the substituted pyrazole derivative (2).

The substituted pyrazole derivative is suitable for use as an active ingredient of pharmaceuticals for the treatment of cancer, e.g., leukemia, melanoma, lung cancer, colon cancer, brain cancer, ovarian cancer, breast cancer, prostate cancer, kidney cancer, and/or hepatic cancer. As described in detail in the following examples, the substituted pyrazole derivative demonstrated effective anticancer activity, with no marked acute toxicity. The substituted pyrazole derivative demonstrates higher potency in providing anti-cancer relief ($GI_{50}$: 3.59 µM) compared to the reference standard, sorafenib.

The substituted pyrazole derivative can be administered by any conventional route of administration, including, but not limited to, intravenous, oral, subcutaneous, intramuscular, intradermal and parenteral. Forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

A pharmaceutical composition can include the substituted pyrazole derivative, or salt thereof, and a pharmaceutical carrier. Carriers are inert pharmaceutical excipients, including, but not limited to, binders, suspending agents, lubricants, flavorings, sweeteners, preservatives, dyes, and coatings. The composition can be presented in a form suitable for daily, weekly or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the substituted pyrazole derivative or an amount effective to treat cancer may be determined from in vivo assays described herein.

The present teachings are illustrated by the following examples. Melting point was measured using open capillary tubes using a Griffin apparatus, and is uncorrected. IR spectra were recorded on a Shimadzu 435 IR Spectrophotometer (v, cm$^{-1}$) using potassium bromide (KBr) discs. $^1$H and $^{13}$C NMR spectra were recorded on Brucker 500 MHz NMR Spectrophotometer using DMSO-$d_6$ as the solvent and the chemical shifts were measured in ppm, relative to trimethylsilane (TMS) as an internal standard. Mass spectra were recorded on a Hewlett Packard 5988 Spectrometer. Elemental microanalyses data (C, H, and N) were found within the agreeable limits of the calculated values (within ±0.4% of the theoretical values). TLC-analysis was carried out on silica gel 60 $F_{254}$ aluminum plates for reactions progress, the results of which were visualized using UV lamp.

Example 1

Synthesis of (4Z)-4-((1-(3-Chlorophenyl)-3-(4-methoxyphenyl)-1H-pyrazol-4-yl)methylene)-4,5-dihydro-5-imino-1-phenyl-1H-pyrazol-3-amine (2)

1-(3-chlorophenyl)-3-(4-methoxyphenyl)-1H-pyrazole-4-carbaldehyde was reacted with malononitrile as an active methylene compound in absolute ethanol containing a few drops of piperidine as catalyst, producing 2-((1-(3-chlorophenyl)-3-(4-methoxyphenyl)-1H-pyrazol-4-yl)methylene) malononitrile (1). A mixture of 10 mmol of 2-((1-(3-chlorophenyl)-3-(4-methoxyphenyl)-1H-pyrazol-4-yl)methylene)malononitrile (1) and phenyl hydrazine (10 mmol) in absolute ethyl alcohol (30 mL) with catalytic amounts (a few drops, e.g., about 2-5 drops) of piperidine was then heated under reflux for 5 hours, while the progress of the reaction was monitored by TLC. Upon completion of the reaction, the solid precipitate that formed on cooling was filtered off, dried and recrystallized from methyl alcohol to produce the substituted pyrazole derivative, (4Z)-4-((1-(3-chlorophenyl)-3-(4-methoxyphenyl)-1H-pyrazol-4yl)methylene)-4,5-dihydro-5-imino-1-phenyl-1H-pyrazol-3-amine (2). Yield: 74%, mp. 115-117° C.; IR (KBr, cm$^{-1}$) v: 3317 (br., NH, NH$_2$), 1598 (C=C); $^1$H NMR (500 MHz, DMSO-$d_6$): δ 3.80 (s, 3H, OCH$_3$), 6.67-6.70 (m, 2H, H-i, 1), 7.00-7.06 (d, 2H, H-j, n), 7.15-7.19 (m, 2H, H-k, m), 7.36 (d, 2H, H-f, g, J=3), 7.50-7.66 (m, 3H, H-b-d), 7.89 (s, 1H, H-a), 7.95 (d, 2H, H-e, h, J=3), 8.93 (s, 1H, CH of pyrazole), 10.18 (s, 3H, NH and NH$_2$ exchangeable with D$_2$O); $^{13}$C NMR (125 MHz, DMSO-$d_6$): δ 56.19, 104.58, 112.26, 114.50, 117.34, 118.76, 120.12, 123.85, 124.17, 125.94, 127.51, 128.45, 130.12, 131.26, 134.68, 138.46, 141.09, 145.83, 151.28, 153.10, 161.35, 163.73; MS: [m/z, 468 (0.79, M$^+$)]; Anal. Calcd for $C_{26}H_{21}ClN_6O$ (468.5): C, 66.59; H, 4.51, N, 17.92% Found: C, 66.57; H, 4.46; N, 17.89%.

Example 2

In Vitro Anticancer Screening of (4Z)-4-((1-(3-Chlorophenyl)-3-(4-methoxyphenyl)-1H-pyrazol-4-yl)methylene)-4,5-dihydro-5-imino-1-phenyl-1H-pyrazol-3-amine (2)

Anticancer evaluation of the newly synthesized compound was performed by a screening in vitro with 60 human cell lines for primary anticancer screening, representing leukemia, melanoma and cancers of the lung, colon, brain, ovary, breast, prostate and kidney. The screening was a two-stage process, beginning with the evaluation of all compounds against the 60 cell lines at a single-dose of 10 µM. The one dose mean graphs of the selected compound exhibited significant growth inhibition against the 60 cell lines. Therefore this compound passed on to further evaluation at five concentration levels ranging from 0.01 µM to 100 µM. The target compound or the 5-imino-1-phenyl-1H-pyrazol-3-amine derivative (2) demonstrated potency towards most cancer cell lines (median growth inhibitory concentration ($GI_{50}$) mean-graph mid-points (MG-MID)= 3.59 µM) in comparison to the standard drug sorafenib ($GI_{50}$ MG-MID=1.90 µM), see Tables 1 and 2.

tion and regeneration. The aspartate transaminase (AST), alanine transaminase (ALT), alkaline phosphatase (ALP), and total bilirubin (Bili) kits were obtained from Bio-Mérieux (France).

Acute toxicity of the target compound was determined in vivo according to previously reported methods in the literature. Briefly, animals were divided into groups of 10 rats each, and administered single intravenous (IV) doses, graded ranging from 0 to 1200 µg/kg, of the synthesized compound. Control animals received vehicle alone (dimethyl sulfoxide, DMSO).

The mortality of the animals was monitored for up to 1 month posttreatment. The median lethal dose ($LD_{50}$) of the compound was determined as the dose that resulted in 50% mortality of the animals, and was calculated using a com-

TABLE 1

Median growth inhibitory concentrations ($GI_{50}$, µM) of in vitro subpanel tumor cell lines and $GI_{50}$ (µM) full panel mean-graph mid-points (MG-MID) of the target compound in comparison with sorafenib.

| | Subpanel tumor cell lines | | | | | | | | |
|---|---|---|---|---|---|---|---|---|---|
| Cpd. No. | Leukemia | Lung | Colon | CNS | Melanoma | Ovarian | Renal | Prostate | Breast | $GI_{50}$ MG-MID[a] |
| 2 | 0.61 | 7.39 | 1.25 | 5.70 | 2.83 | 6.11 | 5.55 | 0.69 | 2.13 | 3.59 |
| Sorafenib | | | | | | | | | | 1.90 |

[a]$GI_{50}$ full panel mean-graph midpoint (µM).

TABLE 2

Selectivity ratio for the target compound towards the nine tumor cell lines.

| | Subpanel tumor cell lines | | | | | | | | |
|---|---|---|---|---|---|---|---|---|---|
| Cpd. No. | Leukemia | Lung | Colon | CNS | Melanoma | Ovarian | Renal | Prostate | Breast |
| 2 | 5.86 | 0.49 | 2.86 | 0.63 | 1.27 | 0.59 | 0.65 | 5.19 | 1.68 |

Example 3

In Vivo Toxicity and Anticancer Screening of (4Z)-4-((1-(3-Chlorophenyl)-3-(4-methoxyphenyl)-1H-pyrazol-4-yl)methylene)-4,5-dihydro-5-imino-1-phenyl-1H-pyrazol-3-amine (2)

The care and handling of the experimental animals were conducted according to the guidelines set by the World Health Organization (WHO), Geneva, Switzerland. Approval for the study was obtained from the Ethics Committee for Animals Care at the National Research Center, Egypt (Ethic No. 10-230).

Adult male Sprague-Dawley rats (180±20 g, body weight), were purchased from the animal house of the National Research Centre, Egypt. They were maintained for 1 week under environmentally controlled conditions (constant temperature, 25-27° C., with 12-hour light/dark cycles) for 1 week prior to starting the experiments. The mice were housed with 10 animals per cage, and were provided with tap water and commercial diets.

Diethylnitrosamine (DENA) and carbon tetrachloride ($CCl_4$) were purchased from Sigma-Aldrich Chemical Corp., (St. Louis, Mo., USA). The DENA was dissolved in normal saline and injected as a single dose (200 mg/kg, intraperitoneally, i.p.) to initiate hepatic carcinogenesis. The $CCl_4$ was administered as a single dose (2 ml/kg) by gavage as a 1:1 dilution in corn oil to stimulate liver cell proliferaputer program for probit analysis. The compound exhibited good acute toxicity results, and was then further examined for effect on DENA-induced liver cancer in rats. Acute toxicity was considered by the in vivo assay. The results revealed that the target compound, 4-(5-iminopyrazol-3-amine) derivative (2), showed no marked acute toxicity. The test compound (Compound (2)) concentration required for 50% mortality of the animals ($LD_{50}$) was found to be 195 µg/kg body weight.

Adult male Sprague-Dawley rats were divided into groups of eight animals each. Group 1 rats (untreated control) were fed a standard diet and given water throughout the experiment. Group 2 rats (treated with DENA) were injected with a single dose of DENA (200 mg/kg, i.p.), and 2 weeks later received a single dose of $CCl_4$ (2 ml/kg) by gavage as 1:1 dilution in corn oil. Group 3 rats (treated with DENA and target compound) consisted of rats that were treated as the rats in Group 2, but also were treated with target compound administered IV at a dose that was 1/10 the $LD_{50}$, for 10 consecutive days.

At the end of the treatment protocol on day 30 after the last injection, the animals were anesthetized with ether, and blood samples were drawn from the orbital venous plexus. The serum was separated by centrifugation for 5 minutes at 1500 g, and stored at −20° C. until analyzed. This serum was used to determine the liver function by assaying the ALT, AST, and ALP activities and total bilirubin spectrophotometrically according to the manufacturer's instructions using reagent kits obtained from Roche Diagnostics (Mannheim, Germany). Liver function was measured, comparing results for control rats with results in DENA-treated and in target compound-treated rats. The results were reported as mean±standard error of the mean (SE). Statistical significance was analyzed using a one-way analysis of variance (ANOVA) followed by the Student's t-test, while the differences were considered to be significant at p<0.05. Serum obtained from tumor bearing rats showed significant increase in activities of AST, ALT and ALP along with significant (p<0.05) increase in bilirubin level compared to control animals. As shown in Table 3, the elevation of these enzyme activities was indicative of the toxic effect of DENA on the liver tissue.

TABLE 3

Liver function of normal, DENA-treated, and target compound/DENA-treated rats

| Parameter | Control | DENA | Target compd. |
|---|---|---|---|
| AST (U/L) | 56.00 ± 5.2 | 110.00 ± 7.8[a] | 70.00 ± 7.2[b] |
| ALT (U/L) | 38.00 ± 3.7 | 95.00 ± 7.0[a] | 49.00 ± 4.6[b] |
| ALP (U/L) | 110.00 ± 9.3 | 215.00 ± 15.7[a] | 124.00 ± 12.00[b] |
| Bili (mg/dl) | 1.40 ± 0.11 | 2.90 ± 0.20[a] | 1.63 ± 0.16[b] |

Data are expressed as Mean ± S.E. (n = 8) [a] and [b] indicated significant difference from normal control and from DENA-treated rats at p < 0.05 respectively.

It is known that N-nitroso compounds act as strong carcinogens in various mammals including primates. DENA has been shown to be metabolized by cytochrome P-450 IIE1 (CYP 2E1) to its active ethyl radical metabolite, which could interact with DNA causing mutation and carcinogenesis. The subsequent treatment with the target compound at a dose of 1/10 of the $LD_{50}$ values in the rats resulted in substantial normalization in AST, ALT and ALP activities as well as the total bilirubin level, compared to DENA-treated rats, see Table 3. Such a reversal in serum enzyme activities could be attributed to the target compound's ability to inhibit CYP 2E1 activity, presumably by serving as a competitive inhibitor and thereby leading to a decrease in the formation and/or bioactivation of these nitrosamines.

Example 4

Histopathological Examination

For the histopathological examination, the animals were euthanized by decapitation and their livers were rapidly excised, weighed, and washed with saline. Portions of the livers were fixed in 10% formalin in saline, embedded in paraffin wax, serially sectioned, and stained. A standard method of hematoxylin and eosin (H&E) staining was also used.

Figure 3:
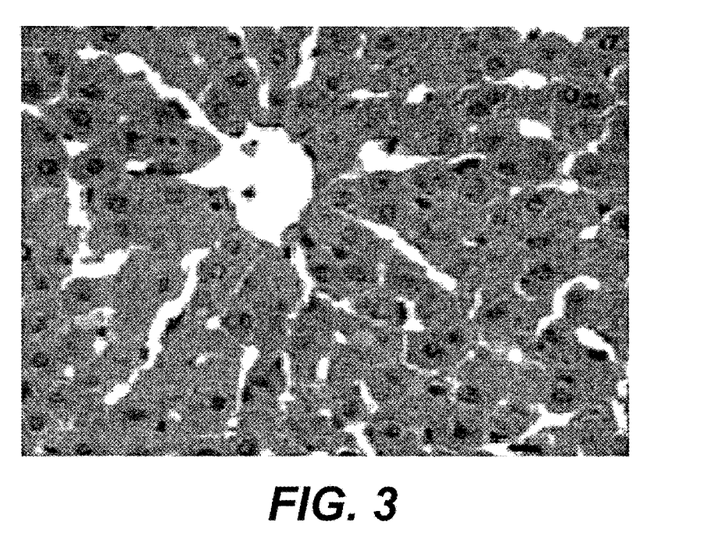
FIG. 3 shows a photomicrograph of a liver section of untreated normal control rats showing unremarkable pathological changes (H&E, 400×).

The results of the histological examination of rat liver sections were consistent with the results from the biochemical studies. The livers of control animals, as exemplified in FIG. 3, exhibited normal architecture characterized by polyhedral shaped hepatocytes and cytoplasm granulated with small uniform nuclei. Hepatocytes were arranged in well-organized hepatic cords and separated by narrow blood sinusoids.

Figure 4:
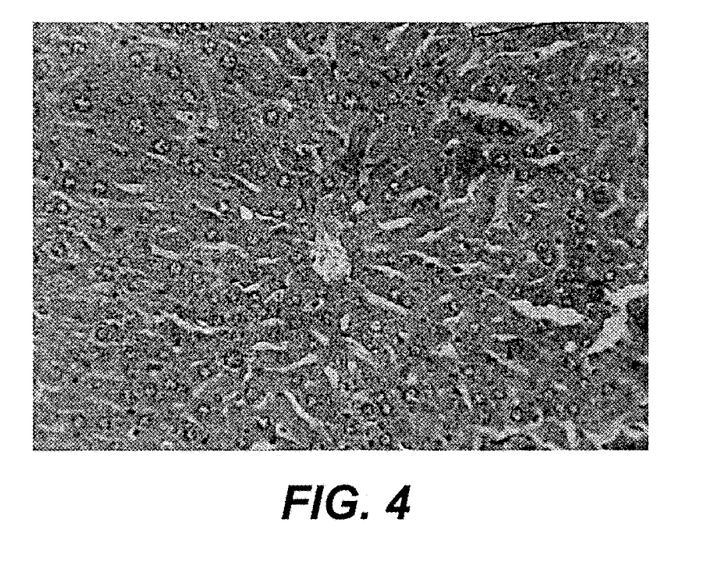
FIG. 4 shows a photomicrograph of a liver section from rats treated with diethylnitrosamine (DENA), showing hyperchromatism, hyperplasia, proliferating hepatocytes (H&E, 200×).
Figure 5:
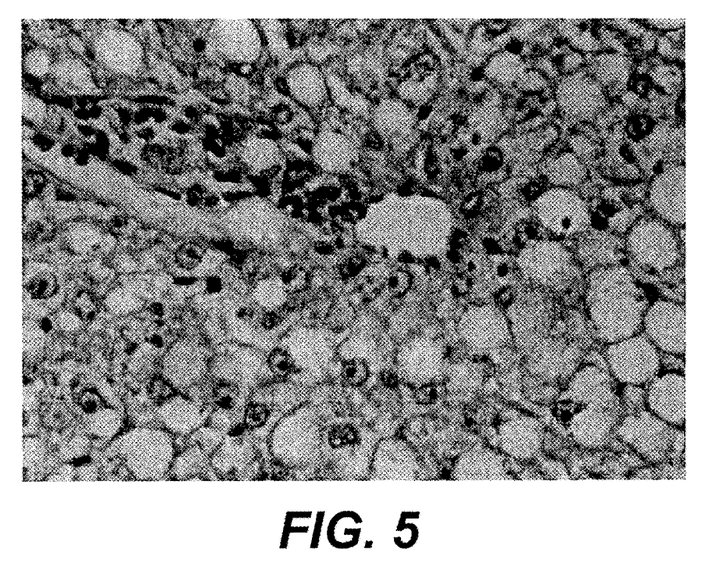
FIG. 5 shows an animal liver section treated with DENA, revealing lost architecture: both hepatic and portal with significant tumor thrombi within portal vessels; tumor cells are slightly larger having more irregular nuclei and numerous mitotic figures (H&E, 400×).
Figure 6:
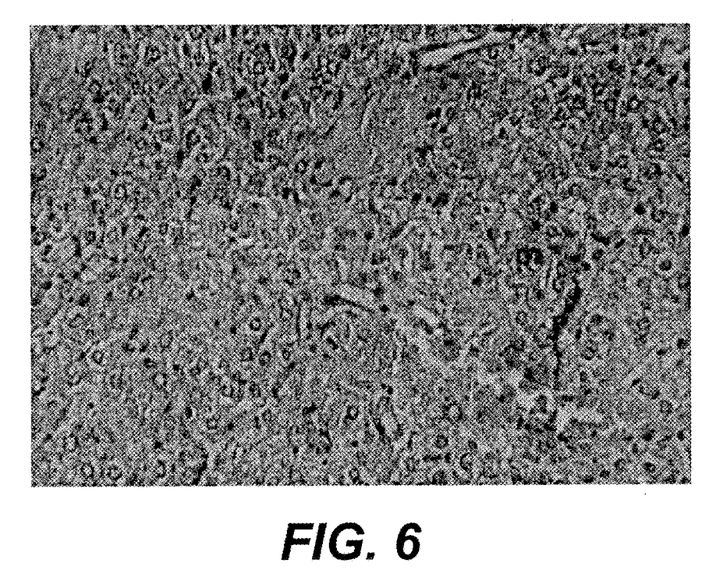
FIG. 6 shows a liver section from an animal treated with DENA, showing megalocytosis, hyperchromatic nuclei, nuclear vesiculation, and nuclear prominence (H&E 200×).

The livers of rats treated with DENA alone showed distortion in the tissue organization, with hyperchromatism, hyperplasia, and proliferating hepatocytes as shown in FIG. 4. These livers exhibited loss in architecture, both hepatic and portal, with significant tumor thrombi within portal vessels. The tumor cells are slightly larger, and have more irregular nuclei and numerous mitotic figures, see FIG. 5. Some sections showed megalocytosis, and hyperchromatic nuclei, as well as nuclear vesiculation and nuclear prominence, see FIG. 6.

Figure 7:
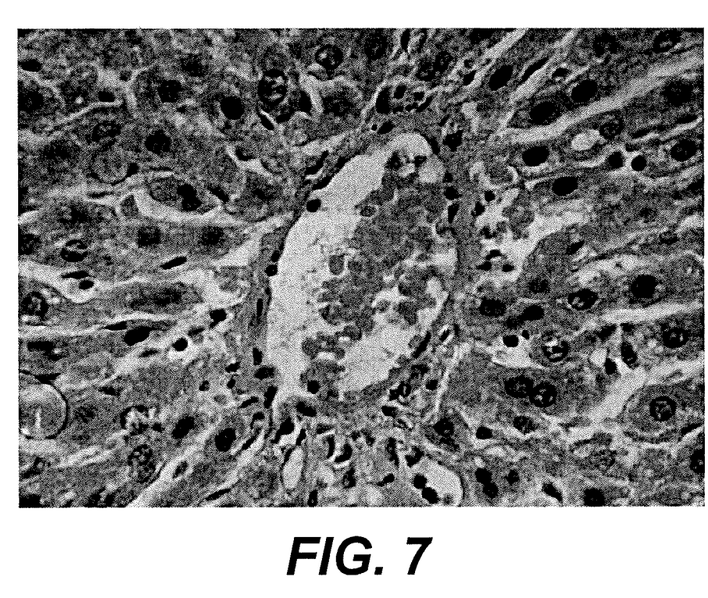
FIG. 7 shows a liver of the DENA-rats treated with the target compound, revealing normal hepatic architecture with the central vein lying at the center of the hepatic lobule surrounded by the hepatocytes as previously seen in normal liver of control rats (H&E 200×).

These marked changes in the hepatic architecture could be explained on the basis that DENA treatment manifested its toxic effects on the generation of Reactive Oxygen Species (ROS) mediators associated with liver damage. The resulting effect was the production of elevated amounts of malondialdehyde (a marker for oxidative stress) and conjugated dienes, which cause deleterious effects on the membranous components of hepatocytes. Livers of the DENA-rats treated with the target showed improvement in the hepatic pattern associated with normal hepatic architecture with the central vein lying at the center of the hepatic lobule surrounded by the hepatocytes FIG. 7.

Example 5

Molecular Modeling

The target compound was constructed into a 3D model using the builder interface of the MOE program. After confirming structure and the formal charges on atoms by 2D depiction, the following steps were carried out: the target compound was subjected to a conformational search and all conformers were subjected to energy minimization. The minimizations were performed with MOE until a RMSD gradient of 0.01 Kcal/mole and RMS distance of 0.1 Å with MMFF94X force-field, and the partial charges were automatically calculated. The obtained data base was saved as an MDB file used in the docking calculations.

The X-ray crystallographic structure of $^{V600E}$B-Raf receptor complexed with SB-590885 (PDB ID: 2FB8) was obtained from the Protein Data Bank through the internet. The enzymes were prepared for docking studies as follows: the ligand molecule SB-590885 was removed from $^{V600E}$B-Raf receptor active sites. Hydrogen atoms were added to the system with their standard geometry. The atomic connections and types of connection were checked for any errors with automatic correction. Selection of the receptor and atom potential were fixed. MOE Alpha Site Finder was used for the active site search in the enzyme structure using all default items. Dummy atoms were created from the obtained alpha Spheres.

Example 6

Docking of the Target Molecule to the Progesterone Receptor Active Sites

Docking of the conformation database of the target compound was done using MOE-Dock software. The following methodology was generally applied: the enzyme active site file was loaded and the Dock tool was initiated. The program specifications were adjusted as follows: Dummy atoms as the docking site; Triangle matcher as the placement methodology to be used; London dG as scoring methodology to be used, adjusted to its default values. The MDB file of the ligand to be docked was loaded and Dock calculations were run automatically. The obtained poses were studied and the poses showing best ligand-enzyme interactions were selected and stored for energy calculations. The 2-dimensional interaction and stereo view for target compound inside the active site of $^{V600E}$B-Raf enzyme were obtained and saved as both MOE and photo files.

Figure 8A:
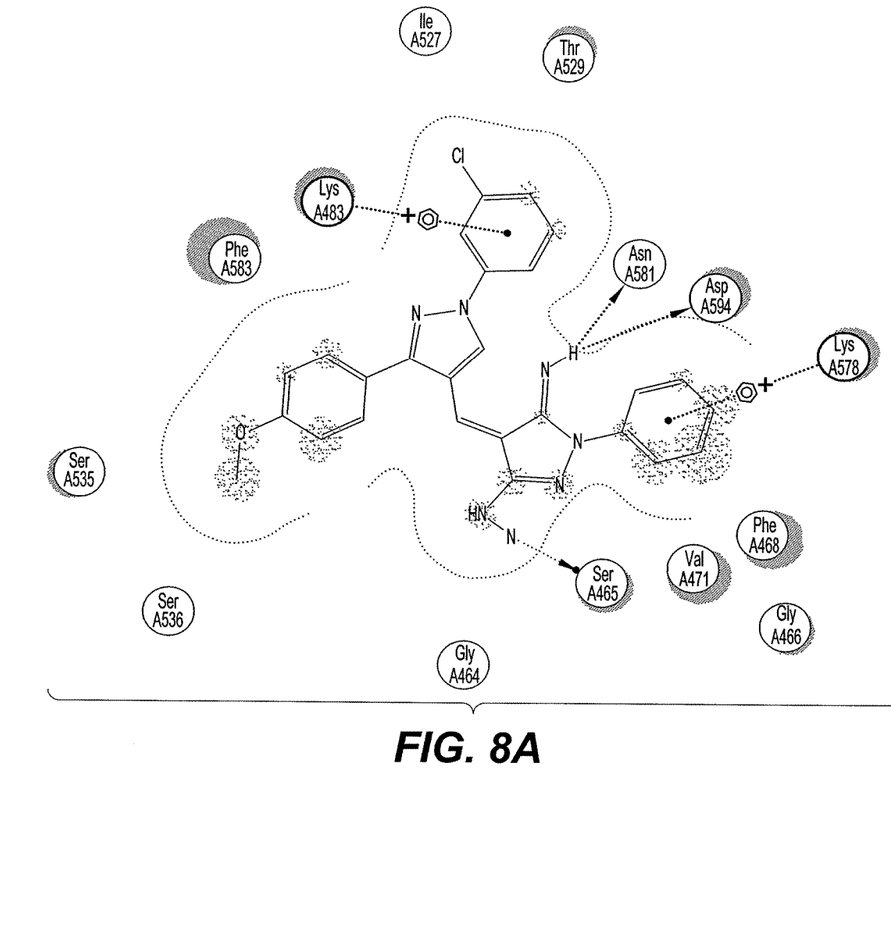
FIG. 8A is a 2-dimensional representation of the proposed binding mode of the target compound, (4Z)-4-((1-(3-chlorophenyl)-3-(4-methoxyphenyl)-1H-pyrazol-4-yl) methylene)-4,5-dihydro-5-imino-1-phenyl-1H-pyrazol-3-amine, in the active site of B-Raf, showing ligand-receptor interactions, with hydrogen bonds illustrated as arrows.
Figure 8B:
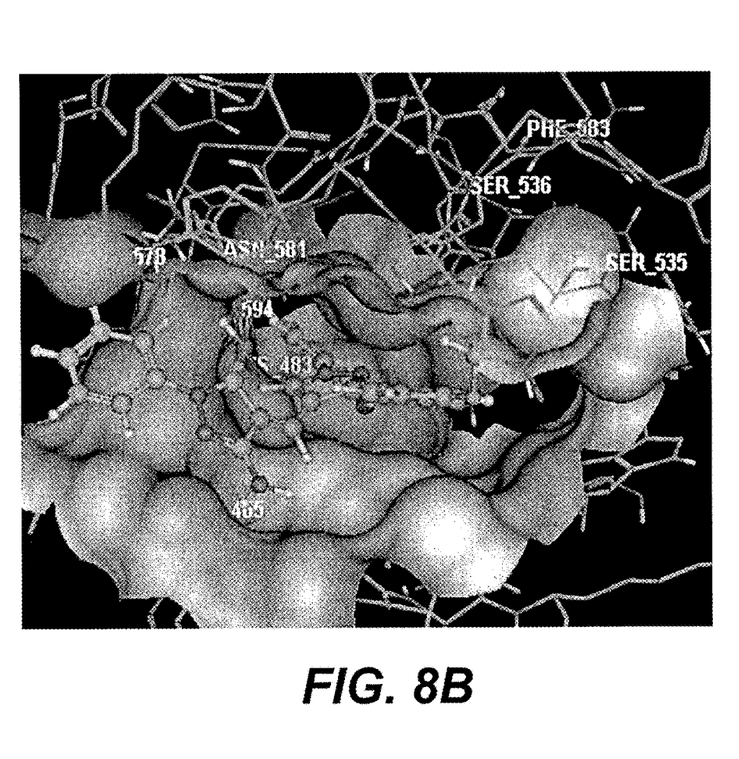
FIG. 8B is a 3-dimensional representation of the binding mode of the target compound, (4Z)-4-((1-(3-chlorophenyl)-3-(4-methoxyphenyl)-1H-pyrazol-4-yl)methylene)-4,5-dihydro-5-imino-1-phenyl-1H-pyrazol-3-amine, situated in the active site of B-Raf.

Docking studies and modeling calculations were performed using the program "Molecular Operating Environment (MOE) version 2008.10." All the interaction energies and calculations were automatically completed. FIGS. 8A and 8B show the proposed binding mode of the target compound docked in the active site of $^{V600E}$B-Raf, in two dimension and three dimension forms, respectively. In FIG. 8A, hydrogen bonds are illustrated as arrows.

The target product was further evaluated at five concentration levels. These compounds were docked into the $^{V600E}$B-Raf active site in order to predict their binding modes, affinities and orientation at the active site of $^{V600E}$B-Raf enzyme. The docking studies reflected in Table 4 show that the target compound interacted with the appropriate amino acids either by hydrogen or ionic bonds. In addition, hydrophobic interaction occurred with most of the important lipophilic amino acids: Lys483, Glu501, Leu514, Leu515, Phe516, Ile527, Thr529, Trp531, Cys532 and Gly534. Lys483, interacting ionically with the m-chlorophenyl of the target compound.

TABLE 4

The docking energy scores of the target compound with the amino acid residues in the ATP-binding site of $^{V600E}$B-Raf forming hydrogen and ionic bonds.

| Compound | Docking score (Kcal/mol) | Amino acid residues (bond length A°) | Atoms involved | Type of bond | CLog P* (O/W) | PSA* (A°)$^2$ |
|---|---|---|---|---|---|---|
| Target Cmpd. | −8.81 | Ser465(2.27); Asn581(2.13); Asp594(2.56); Lys483; Lys578 | H(NH$_2$); H(=NH); H(=NH); m-Cl—Ph; Ph | H H H Ionic Ionic | 5.35 | 92.52 |

The detailed binding mode analyses of the target compound showed the following:

ionic bond: an arene-cation interaction between the centroid of m-chlorophenyl and Lys483;

ionic bond: an arene-cation interaction between the centroid of phenyl and Lys578;

two hydrogen bonds: formed between the imino group of the target compound as hydrogen donor to side chains of the amino acids, acidic Asp594 and Asn581;

a third hydrogen bond: formed between the NH$_2$ group of the target compound as hydrogen donor to the backbone of Ser465; and hydrophobic interactions between the centroid of m-chlorophenyl and the amino acids Ile527 and Thr529.

Figure 9:
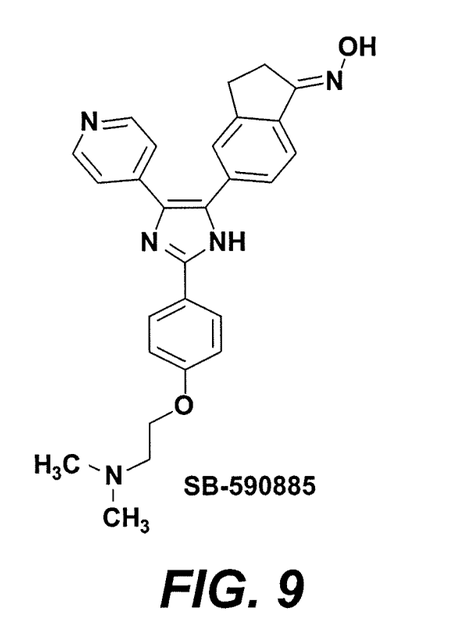
FIG. 9 is the chemical structure of ligand SB-590885.

Docking studies also were conducted to compare the configuration of the target compound and ligand SB-590885, when co-crystallized with $^{V600E}$B-Raf. The chemical structure of ligand SB-590885 is shown in FIG. 9.

Superimposition of the co-crystallized ligand SB-590885 in the active site of $^{V600E}$B-Raf with the target compound co-crystallized in the active site, further supported the conclusion that the target compound can bind in the active site of this enzyme in a similar manner as the ligand binds in the same active site.

Accordingly, the biochemical and histological data and results listed and discussed above demonstrate that the target compound may prove to be a potent anticancer and/or antitumor agent.

It is to be understood that the substituted pyrazole derivatives as anticancer or antitumor agents is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of preparing a substituted pyrazole derivative of the formula:

or a pharmaceutically acceptable salt thereof, the method comprising:

reacting 1-(3-chlorophenyl)-3-(4-methoxyphenyl)-1H-pyrazole-4-carbaldehyde with a first reaction mixture to form a first compound, wherein the first reaction mixture includes malononitrile, and reacting the first compound with a second reaction mixture to provide the substituted pyrazole derivative, wherein the second reaction mixture includes phenyl hydrazine.

2. The method of claim 1, wherein the first reaction mixture further comprises an alcohol and piperidine.

3. The method of claim 2, wherein the alcohol is ethanol.

4. The method of claim 3, wherein the ethanol is absolute ethanol.

5. The method of claim 2, wherein the second reaction mixture further comprises an alcohol and piperidine.

6. The method of claim 5, wherein the alcohol in the second reaction mixture is ethanol.

7. The method of claim 6, wherein the ethanol is absolute ethanol.

8. The method of claim 7, wherein the first compound is 2-((1-(3-chlorophenyl)-3-(4-methoxyphenyl)-1H-pyrazol-4-yl)methylene)malononitrile.

9. The method of claim 8, wherein the first compound and the second reaction mixture are heated under reflux until the reaction completes.

10. The method of claim 9 wherein the first compound and the second reaction mixture are heated for about 5 hours.

11. A method of preparing a substituted pyrazole derivative, having the formula or a pharmaceutically acceptable salt thereof, the method comprising:

reacting 1-(3-chlorophenyl)-3-(4-methoxyphenyl)-1H-pyrazole-4-carbaldehyde with a first reaction mixture to form 2-((1-(3-chlorophenyl)-3-(4-methoxyphenyl)-1H-pyrazol-4-yl)methylene)malononitrile, wherein the first reaction mixture includes malononitrile, and reacting the 2-((1-(3-chlorophenyl)-3-(4-methoxyphenyl)-1H-pyrazol-4-yl)methylene)malononitrile with a second reaction mixture to provide the substituted pyrazole derivative, wherein the second reaction mixture includes phenyl hydrazine.

12. The method of claim 11, wherein the first reaction mixture further comprises absolute ethanol and piperidine.

* * * * *